US00PP08576P

United States Patent [19]

Klemm

[11] Patent Number: Plant 8,576

[45] Date of Patent: Feb. 1, 1994

[54] GERANIUM NAMED KLEFIFIEST

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 952,943

[22] Filed: Sep. 28, 1992

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new and novel Geranium plant particularly distinguished by its fresh pink color. The pink colored florets form medium-size ball-shaped umbels, having between about 40–50 florets form the medium-sized ball-shaped umbel. The medium-shaped flower umbels are long lasting and are supported by strong, upright 25 cm stalks, whose foliage is bushy and Botrytis-resistant.

1 Drawing Sheet

BACKGROUND OF THE NEW PLANT

This Geranium cultivar originated as a hybrid seedling produced in my nursery at Stuttgart, Germany by my crossing of two plants, hereinafter identified, selected from a field of various Geranium varieties maintained at my nursery for breeding purposes. This particular seedling was selected from those produced by the said hybridization because of the very unusual flower coloration on a plant having abundant foliage and very favorable growth characteristics. This selected seedling was propagated by me at Stuttgart by cuttings with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new Geranium plant is illustrated by the accompanying photographic drawing which, in full color, shows the form and coloration of the flowers as they appear. The colors shown are as nearly true to these herein specified as is reasonably possible to obtain by conventional photographic procedures.

DESCRIPTION OF THE NEW PLANT

The following is a detailed description of my new Geranium plant as observed from plants grown under greenhouse conditions in Stuttgart, Germany with the stated flower colors being according to The R.H.S. Colour Chart of The Royal Horitcultural Society of London, England.

THE PLANT

Origin: Seedling.

Parentage:

*Seed parent.*—Doppia. Commercially unavailable. Doppia has dark green foliage and a well-filled flower. It has good compact growth and is dark pink in color.

*Pollen plant.*—Penja. PAC Jade, available in Dresden. It has an early white flower and because of this early flower, it is a small plant. Penja has light green leaves.

These parent plants are so identified in my business records of the present cultivar maintained at the office of the Stuttgart nursery and the production of the stated cross and the selection of Kleflam are also recorded at the same facility.

Classification:

*Botanic.*—Geranium hybrid.

*Commercial.*—Zonal Geranium.

Form: An upright bush having a medium spreading growth habit.

Height: About 250 mm.

Branching character: Self-branching without pinching. Klefifiest is self-branching because it builds up a compact bush with many stems and a canopy that covers the whole pot and hides the stems.

Flower stem:

*Length.*—17 to 18.5 cm.

*Strength.*—Erect.

*Color.*—Dark green.

Foliage:

*Quantity.*—45 to 55 leaves. This number is high due to the compact growth of Klefifiest Internode length: 9–16 mm.

*Size and shape of leaf.*—The size is 55 m×55 mm to 55 mm×60 mm. Most of the leaves are 50 mm×55 mm large. The shape is a little bit like an Ivy leaf with main parts, made by deep crenations. Following the deep crenations are small becrenations. The leaves are almost closed. There is a very, very light zonation on the very young leaves.

*Margin type.*—Bicrenate.

*Texture.*—Smooth.

*Color.*—Top surface:RHS 137-A with darker zonations. Bottom surface: RHS 137-B with lighter veins.

Petioles:

*Length.*—Floret petiole: 22 mm to 27 mm. Leave petiole: 40 mm to 65 mm.

THE BUD

Size:

*Shape.*—Ovoid.

*Diameter.*—11 mm.

*Length.*—13 mm.

*Color of petals.*—Very light pink when sepals first divide and pink when petals begin to unfurl.

Sepals:

*Shape.*—Pointed.

*Color.*—Inside — green. Outside — dark green.

Calyx:

*Shape.*—Cup-shaped.

*Aspect.*—Slightly hairy.

*Size.*—Broad.

FLOWER

Blooming season: Continuous and profuse from spring to fall.

Size of flower: Medium.

*Diameter.*—About 45 mm.

*Depth.*—About 10 mm.

Borne: Singly one per pedicel; in an umbel cluster.

Shape: Cup-shaped.

Florets:

*Number.*—40–50 per cluster.

*Diameter.*—45×53 mm.

Petalage:

*Number of petals.*—6–8 per floret.

*Arrangement.*—Imbricated.

Form: Broad with entire and round apex margin.

Texture: Soft.

Appearance: Shiny.

Color:

*Outer petal.*—Body RHS 55A, base RHS 55A.

*Reverse side.*—RHS 52C and RHS 55B-C.

*Inside petal.*—Body RHS 62A, base RHS 62A.

*Reverse side.*—RHS 52C and RHS 55B-C.

Discoloration after full bloom: No.

Disease resistance: Botrytis flower and leave.

Lasting quality:

*On the plant.*—About 30 days.

*As cut flower.*—About 5–6 days.

Pruning or training requirements: None. The claimed Geranium is cultivated according to the following procedure. Propagation is begun at week 2. Potting takes place in week 6. The plant is placed in 12 cm pots. The soil at that time has a pH of 6 and a EC of 1,3 to 1,4. The plant is not pinched and not treated with Cycocel. Fertilizing begins at week 7 and is performed 5 times until week 15. Starting at week 6, the daily medium temperature in the room where the plant is maintained is set to 17° C. This is continued until week 11. In week 12, the temperature is lowered to 16° C. The following week, on a cool morning, two hours before sunrise, the room temperature is lowered an additional 6 degrees Celsius for 7 hours.

Petaloids:

*Number.*—One to four.

*Color.*—RHS 68A.

THE REPRODUCTIVE ORGANS

Stamens:

*Number.*—Seven.

*Arrangement.*—In a ring around the pistil.

*Anthers.*—Size: About 1.5 mm .

*Filaments.*—Length: About 4 mm. Color: Light pink.

*Pollen.*—Color: Orange.

Pistils:

*Number.*—One.

Styles:

*Length.*—About 7 mm.

*Stigmas.*—White to pink.

Character of ovaries: Normal.

FRUIT

Fertility: The fruit is fertile.

Shape: Ovoid.

Color at maturity: Dark brown.

I claim:

1. A new and distinctive hybrid Geranium plant substantially as herein shown and described, characterized in particular by its medium ball-shaped fresh pink flower clusters, which are long lasting.

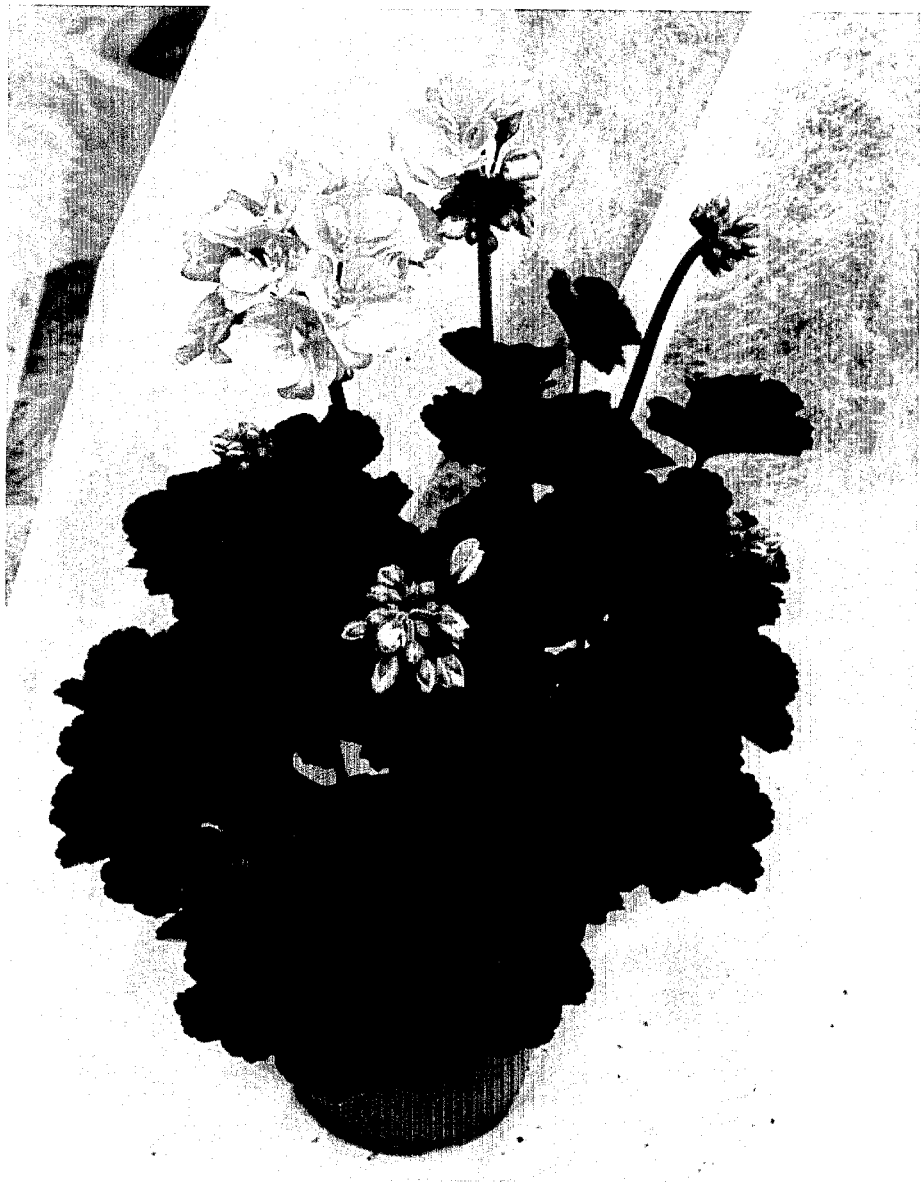

* * * * *